US00PP12875P2

(12) United States Plant Patent
Salmon

(10) Patent No.: US PP12,875 P2
(45) Date of Patent: Aug. 20, 2002

(54) BRACTEANTHA PLANT NAMED 'FLORABELLA LEMON'

(75) Inventor: Alexander David Salmon, Gapsted (AU)

(73) Assignee: Outback Plants Pty. Ltd., The Patch (AU)

( * ) Notice: Subject to any disclaimer, the term of this patent is extended or adjusted under 35 U.S.C. 154(b) by 0 days.

(21) Appl. No.: 09/840,806

(22) Filed: Apr. 25, 2001

(51) Int. Cl.[7] ..... A01H 5/00
(52) U.S. Cl. ..... Plt./359
(58) Field of Search ..... Plt./359

(56) References Cited

PUBLICATIONS

UPOV–ROM GTITM Computer Database, 2001/06, GTI Jouve Retrieval Software, citation for 'Florabella Lemon'.*

* cited by examiner

*Primary Examiner*—Bruce R. Campell
*Assistant Examiner*—Susan B McCormick
(74) *Attorney, Agent, or Firm*—C. A. Whealy

(57) ABSTRACT

A new and distinct cultivar of Bracteantha plant named 'Florabella Lemon', characterized by its upright, outwardly spreading and rounded plant form; compact plant habit; small lanceolate leaves; light yellow-colored ray florets, and short peduncles that hold inflorescences above the foliage.

1 Drawing Sheet

BACKGROUND OF THE INVENTION

The present invention relates to a new and distinct cultivar of Bracteantha plant, botanically known as *Bracteantha bracteata* and referred to by the cultivar name Florabella Lemon.

The new Bracteantha is a product of a planned breeding program conducted by the Inventor in Gapsted, Victoria, Australia. The objective of the program is to create and develop Bracteantha cultivars with a compact growth habit, small leaves, numerous inflorescences, attractive floret colors, and short peduncles.

The new Bracteantha originated from a cross by the Inventor of a golden yellow ray floret-colored proprietary selection of *Bracteantha bracteata* as the female, or seed, parent with a white ray floret-colored proprietary selection of *Bracteantha bracteata* as the male, or pollen, parent. The new Bracteantha was discovered and selected by the Inventor as a plant within the progeny of the stated cross in a controlled environment in Gapsted, Victoria, Australia in 1997. The selection of the new Bracteantha was based on its light yellow ray florets, compact growth habit, small leaf size and short peduncle length as plants of the new Bracteantha are more compact, have smaller leaves and shorter peduncles than plants of the parent selections.

Asexual reproduction of the new Bracteantha by terminal cuttings taken in a controlled environment in Gapsted, Victoria, Australia, has shown that the unique features of this new Bracteantha are stable and reproduced true to type in successive generations.

The new Bracteantha has not been observed under all possible environmental conditions. The phenotype may vary somewhat with variations in environment such as temperature, daylength, light intensity, photoperiod, and water and nutritional status without, however, any variance in genotype.

The following characteristics have been repeatedly observed and are determined to be basic characteristics of 'Florabella Lemon' and distinguish the new Bracteantha as a new and distinct cultivar:

1. Upright, outwardly spreading and rounded plant form.
2. Compact plant habit.
3. Small lanceolate leaves.
4. Light yellow-colored ray florets.
5. Short peduncles that hold inflorescences above the foliage.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Bracteantha. The photograph comprises a side perspective view of a typical plant of 'Florabella Lemon' grown in a container for about 8 to 10 weeks.

DETAILED BOTANICAL DESCRIPTION

The following observations, measurements and values describe plants grown in Gapsted, Victoria, Australia, under outdoor conditions with day temperatures ranging from 15 to 40° C., night temperatures ranging from 8 to 25° C., and light levels ranging from 5,000 to 9,000 foot candles. Rooted liners of the new Bracteantha were planted in 15-cm containers and grown for about 8 to 10 weeks. Color references are made to The Royal Horticultural Society Colour Chart, 1995 edition, except where general terms of ordinary dictionary significance are used.

Botanical classification: *Bracteantha bracteata* cultivar Florabella Lemon.

Parentage:

*Female or seed parent.*—Unidentified golden yellow ray floret-colored selection of *Bracteantha bracteata*, not patented.

*Male or pollen parent.*—Unidentified white ray floret-colored selection of *Bracteantha bracteata*, not patented.

Propagation:

*Type.*—By cuttings.

*Time to initate roots.*—Summer: About 10 to 20 days at 20 to 25° C. Winter: About 15 to 35 days at 20° C.

*Root description.*—Fine to somewhat fibrous.

Plant description:

*General appearance.*—Upright, outwardly spreading and rounded herbaceous plant with lanceolate foliage and inflorescences held above the foliage on short peduncles. Appropriate for 15 pots to 25-cm hanging basket containers.

*Crop time.*—Moderately fast growth rate; to produce a finished 15-cm containerized plant from rooted cuttings, about 8 to 10 weeks are required.

*Plant height.*—About 30 to 45 cm.

*Plant width.*—About 35 to 45 cm.

*Branching.*—Freely branching, about 15 lateral branches per plant.

*Lateral branch description.*—Length: About 10 to 25 cm. Width: About 4 to 7 mm. Internode length: About 0.9 to 2.3 cm. Texture: Sparsely pubescent; sometimes with very fiant ridges. Color: 143C.

*Foliage description.*—Arrangement: Alternate, single, sessile. Shape: Lanceolate. Margin: Entire; slightly recurved. Apex: Acute. Base: Decurrent, clasping. Length: About 2.8 to 13.2 cm. Width: About 0.3 to 1.8 cm. Texture, both surfaces: Thin, slightly rough; sparsely pubescent. Venation pattern: Pinnate. Color: Young and fully expanded leaves, upper surface: 147A; venation, 144B, Young and fully expanded leaves, lower surface: 147B; venation, 144A.

Flowering description:

*Inflorescence form.*—Daisy-type composite inflorescence form. Inflorescences arranged acropetally on a capitulum.

*Inflorescence longevity.*—Inflorescences last on the plant for about 4 to 6 weeks, about 2 to 3 weeks as a fresh cut flower, and more than 6 weeks as a dried cut flower. Inflorescences persistent.

*Natural flowering season.*—Natural flowering season is spring to fall. Plants flower continuously during this period. Inflorescences close when wet and open when dry.

*Quantity of inflorescences.*—About 1 to 3 inflorescences and about 2 to 5 flower buds per lateral branch.

*Inflorescence aspect.*—Flat to slightly cupped.

*Inflorescence diameter.*—About 3.5 to 4.8 cm.

*Inflorescence depth (height).*—About 1.8 to 2.3 cm.

*Disc diameter.*—About 1.2 to 2.1 cm.

*Fragrance.*—Slight; honey-like.

*Ray florets.*—Appearance: Satiny. Texture: Papery. Aspect: Flat, with subsequent development, slightly reflexed. Shape: Triangular. Margin: Entire. Apex: Acute. Base: Truncate. Length: About 0.8 to 1.8 cm. Width: About 3 to 6 mm. Color: When opening, upper surface: 4B to 4C. When opening, lower surface: 155A to 159C. Mature, upper surface: 3C to 3D; with subsequent development, apex and midsection, 164B to 164D, towards base, 2D. Mature, lower surface: 8D to 162D.

*Disc florets.*—Shape: Tubular with five lobes. Diameter: About 1 mm. Width: About 1 mm. Color: Immature: 145C. Mature: 26A.

*Peduncle.*—Length: About 11.8 to 17.9 cm. Aspect: Erect. Strength: Moderately strong; brittle with young; inflorescences held erect above foliage. Color: Young: 145B. Mature: 146D. Texture: Slightly rough, pubescent.

*Flower bud.*—Shape: Broadly ovoid. Length: About 1.2 to 1.6 cm. Diameter: About 1.2 to 1.6 cm. Color: Towards apex, 158A; towards base, 161D.

*Androecium.*—Present only on disc florets. Stamen number: One per disc floret. Anther shape: Linear. Anther color: 23A. Amount of pollen: Moderate. Pollen color: 23A.

*Gynoecium.*—Present on both ray and disc florets. Pistil number: One per floret. Style length: About 3 mm. Style color: 23C. Stigma shape: Bilobed. Stigma color: 23C.

*Seed.*—Seed production has been observed; seeds typical of species.

Disease/pest resistance: Plants of the new Bracteantha have been observed to be susceptible to White Rust, casual agent *Albugo candida*. Plants of the new Bracteantha have not been observed to be resistant to pathogens and pests common to Bracteanthas.

It is claimed:

1. A new and distinct cultivar of bracteantha plant named 'Florabella Lemon', as illustrated and described.

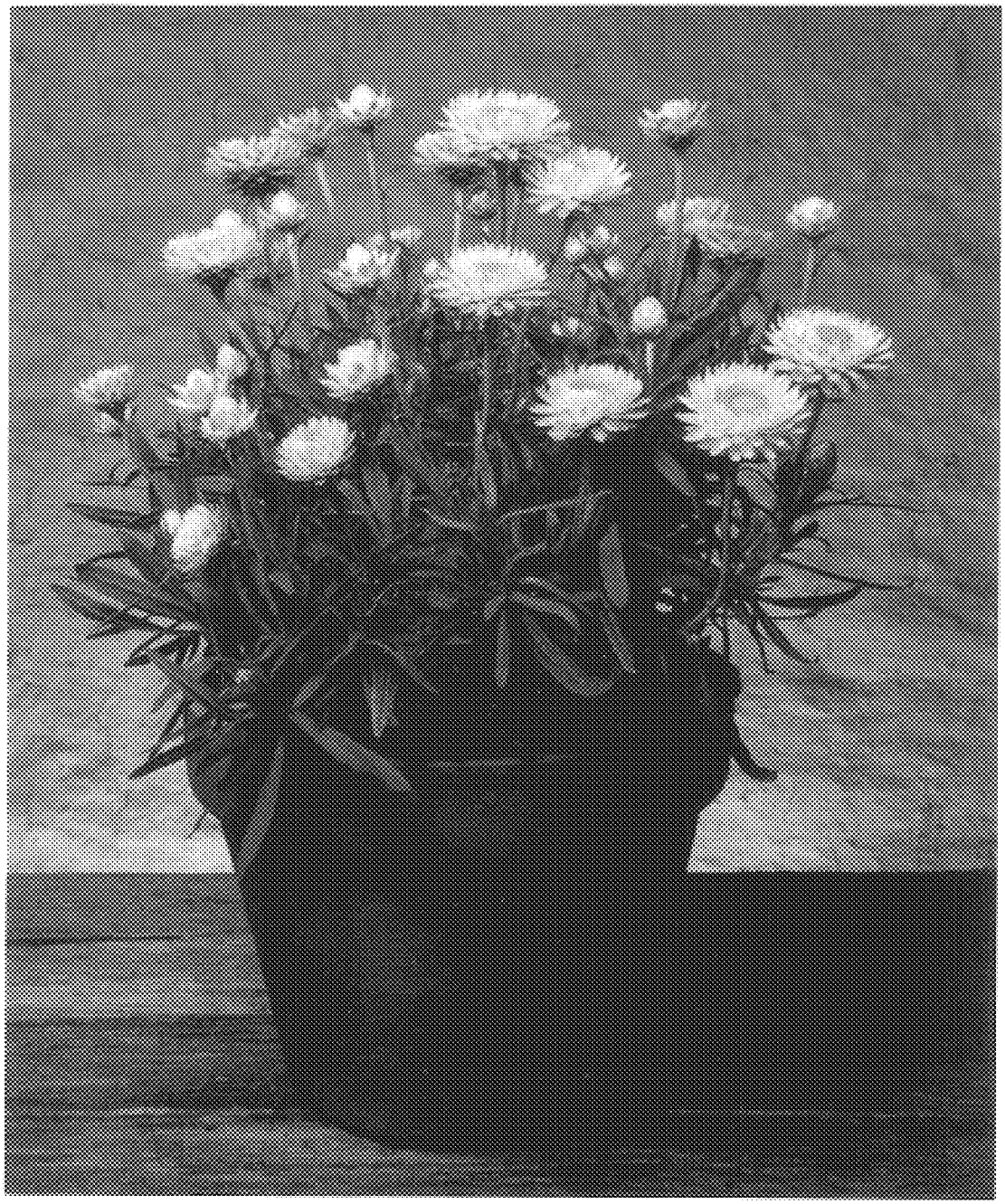

* * * * *